United States Patent [19]

Frey et al.

[11] Patent Number: 5,019,082
[45] Date of Patent: May 28, 1991

[54] RASP-LIKE REAMING INSTRUMENT

[75] Inventors: Otto Frey, Winterthur; Rudolf Koch, Berlingen, both of Switzerland

[73] Assignee: Sulzer Brothers Limited, Winterthur, Switzerland

[21] Appl. No.: 127,208

[22] Filed: Dec. 1, 1987

[30] Foreign Application Priority Data

Jan. 8, 1987 [CH] Switzerland .............. 39/87

[51] Int. Cl.$^5$ ................................ A61F 5/04
[52] U.S. Cl. ................................ 606/85
[58] Field of Search ............... 128/92 VJ, 92 R, 305; 29/76 R, 76 A, 78; 409/244, 259; 407/13, 14, 115; 606/88; 30/123.5, 123.7, 279.6, 287, 351, 355, 357; 241/101 R

[56] References Cited

U.S. PATENT DOCUMENTS

| | | | |
|---|---|---|---|
| D. 272,648 | 2/1984 | Bolesky et al. | D24/28 |
| D. 273,806 | 5/1984 | Bolesky et al. | D24/28 |
| 869,529 | 10/1907 | Smith | 30/279.6 |
| 1,121,126 | 12/1914 | Oakley | 407/13 |
| 1,221,598 | 4/1917 | Roberts | 30/123.5 |
| 1,915,869 | 6/1933 | Rowley | 241/101 |
| 2,482,180 | 9/1949 | Heard | 241/101 |
| 2,984,892 | 5/1961 | Oxford et al. | 29/78 |
| 3,121,450 | 2/1964 | Cronheim | 30/305 |
| 3,829,942 | 8/1974 | Scott | 29/78 |
| 4,671,275 | 6/1987 | Deyerle | 128/92 VJ |

FOREIGN PATENT DOCUMENTS 47701 1/1977 Japan .................. 409/244

Primary Examiner—Robert A. Hafer
Assistant Examiner—Charles H. Sam
Attorney, Agent, or Firm—Kenyon & Kenyon

[57] ABSTRACT

The rasp-like reaming instrument is constructed as a hollow body with exterior teeth and openings adjacent the teeth. During use, bone material which is peeled off by the teeth is directed through the openings into the interior of the body to avoid accumulation of the material under the teeth. The cutting edges of the teeth remain unencumbered during a reaming operation.

9 Claims, 2 Drawing Sheets

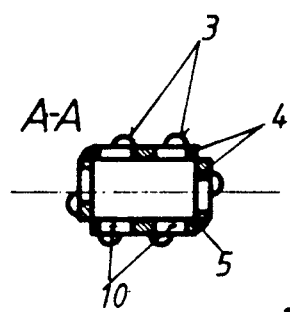
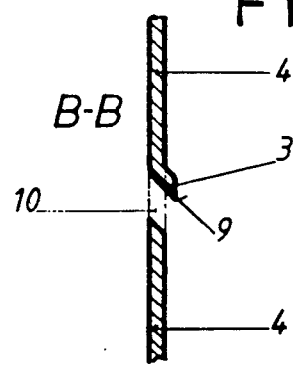
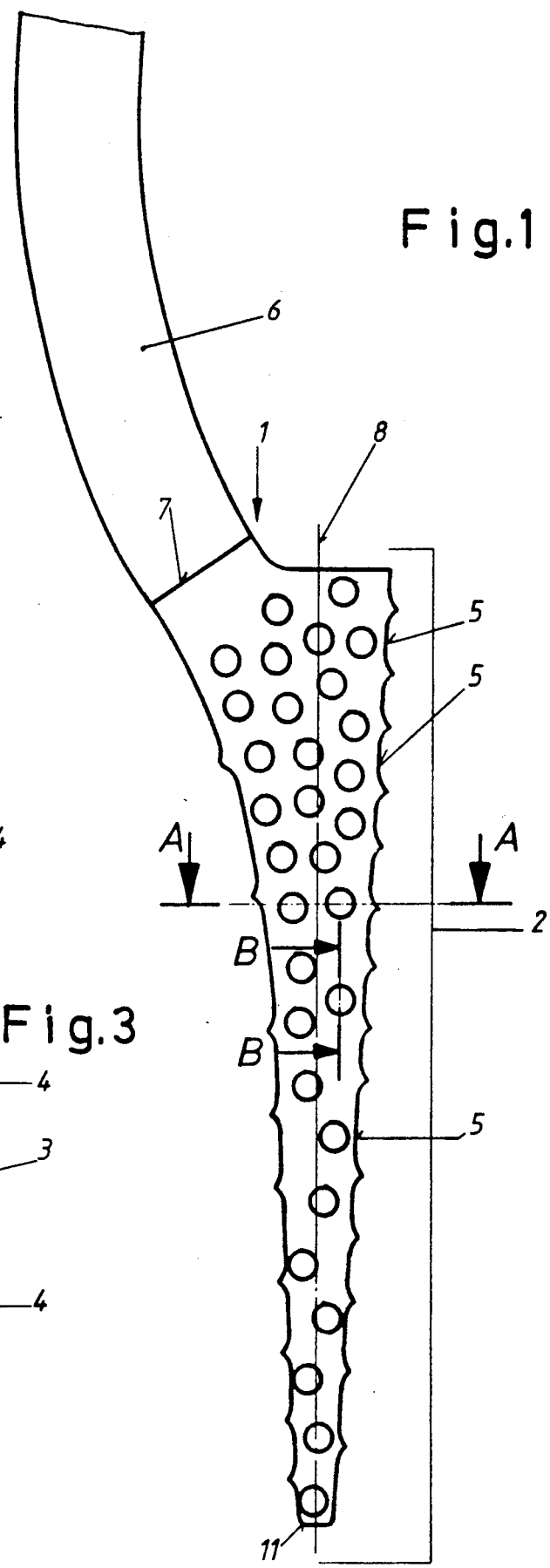
Fig.1
Fig.2
Fig.3

RASP-LIKE REAMING INSTRUMENT

This invention relates to a rasp-like reaming instrument for bones and particularly for the preparation of a long bone for implantation of an implant shaft.

In the past, bone reaming instruments have been formed as solid bodies with dimensions modeled after the implant shaft which is to be implanted and have been provided with cutting edges or teeth on the outer circumference, for example, as described in Swiss Patent 618,865. However, during use of such instruments, the removal of the material peeled off from within a bone cavity has presented difficulties. Generally, the peeled material "clogs up" the teeth or cutting edges after the instrument has been driven into a bone for only a short distance. Consequently, the spongiosa of the bone tissue is no longer scrapped by the teeth but is displaced and compressed as the instrument is driven in further into the bone cavity.

Accordingly, it is an object of the invention to prevent clogging up of the teeth or cutting edges of a reaming instrument.

It is another object of the invention to remove the material which is peeled off from within a bone cavity by a rasp-like reaming instrument in a simplified manner.

It is another object of the invention to reduce the damage to the spongiosa lining a bone cavity to be cleared from implantation of a prosthesis.

It is another object of the invention to minimize damage to the spongiosa lining a hollow space of a bone.

Briefly, the invention provides a rasp-like reaming instrument for bones which is comprised of an elongated hollow body having a plurality of circumferentially disposed openings in the body and a plurality of circumferentially disposed teeth for peeling bone material from within a bone. In addition, each opening is disposed adjacent to a tooth to permit passage of peeled bone material into the hollow body during use of the instrument.

The working region of the instrument which is covered with the teeth is generally formed as a hollow body resembling at least approximately the shape of the shank to be implanted.

When the instrument is driven into a bone, the material scrapped or peeled off by the teeth passes through the openings adjacent the teeth into the hollow interior space of the instrument so that the teeth cannot be clogged up. The major part of this material is then removed when the instrument is withdrawn from the bone cavity.

The instrument can be relatively simply produced by forming the hollow body of a plurality of discrete plates which are welded together along butt edges thereof.

If the length and width of the working region, particularly in the distal region of the instrument, are intended to be variable, the instrument may be composed of two axial parts. Further, clearing can be facilitated if, in a two-part instrument, the distal part is formed as a tooth free guide body. This permits the instrument to be guided in a previously prepared marrow bore while being driven in.

These and other objects and advantages of the invention will become more apparent from the following detailed description taken in conjunction with the accompanying drawings wherein:

FIG. 1 illustrates a side view of a rasp-like reaming instrument constructed in accordance with the invention in approximately actual size;

FIG. 2 illustrates a view taken on line A—A of FIG. 1;

FIG. 3 illustrates a view taken on line B—B of FIG. 1; and

Figure 4:
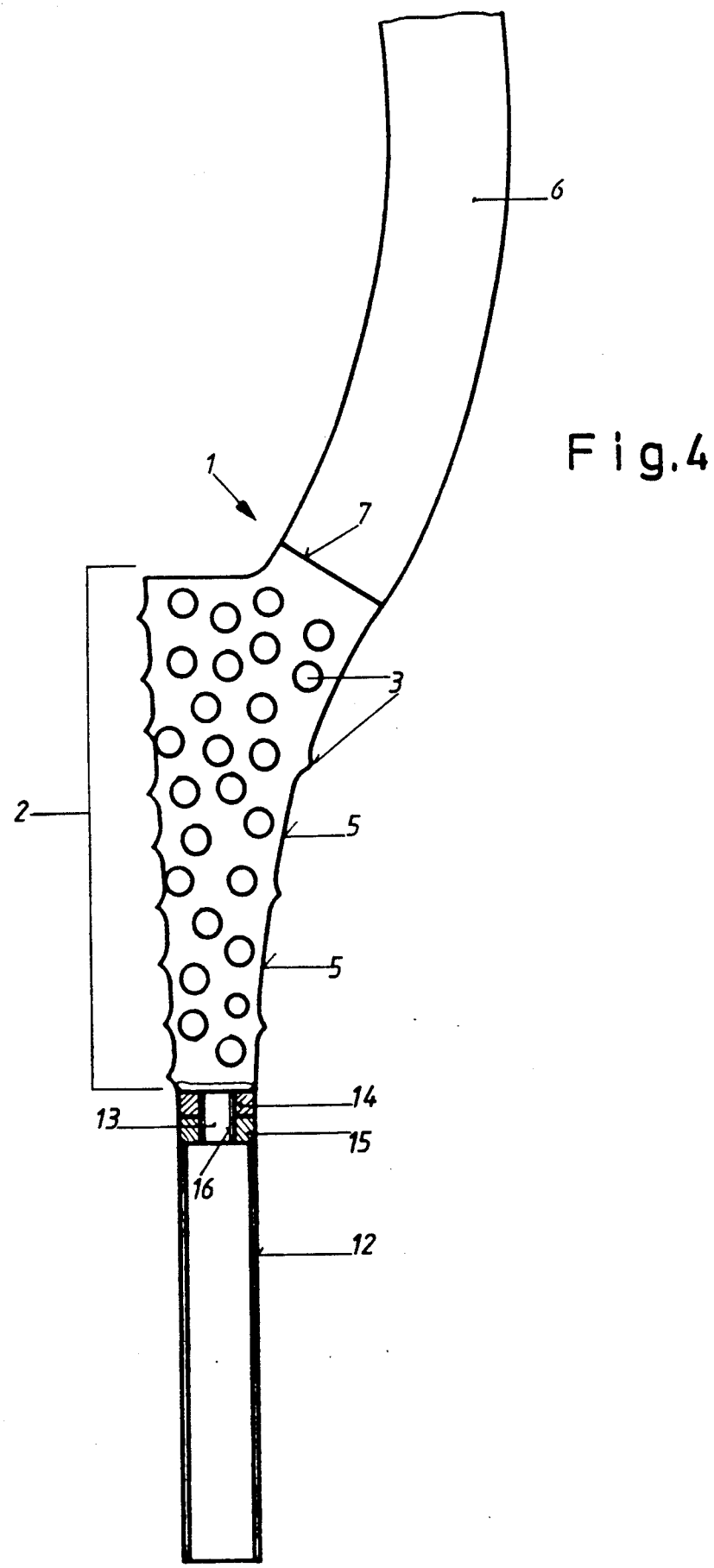
FIG. 4 illustrates a view similar to FIG. 1 of a modified reaming instrument in accordance with the invention.

Referring to FIG. 1, the rasp-like reaming instrument 1 is adapted in shape and dimensions to the shaft of a prosthesis for implantation in a femur. As indicated, the instrument 1 has a working region 2 which is covered with a large number of teeth 3 and which is conically shaped to taper inwardly towards a distal end. This working region 2 is formed as an elongated hollow body of slender shape which, for reasons of manufacture, is formed of a plurality of discrete, essentially planar metal plates 4 which are welded together along butt edges thereof by suitable welds 5 distributed over the length of the region 2. As indicated in FIG. 2, the plates 4 define an essentially rectangular hollow cross section.

Referring to FIG. 1, the upper end, as viewed, of the working region continues as a neck of the instrument to an upper solid part 6 which is secured thereto, for example, via a weld seam 7. This upper part 6 which is of arcuate shape forms an anvil for a driving instrument (not shown). The upper part 6 is shaped so that the effect of the force of the blows of a driving instrument proceeds in the direction of the driving or longitudinal axis 8 of the working region 2.

Referring to FIG. 3, each tooth 3 of the instrument 1 terminates in a sharp cutting edge 9. In addition, each tooth 3 is associated with and is adjacent an opening 10 in the plate 4.

As indicated in FIGS. 1 and 2, the teeth 3 are circumferentially disposed about the body forming the working region 2 and, likewise, the openings 10 are circumferentially disposed in the body with each opening 10 being disposed adjacent a respective tooth 3.

During use, as the instrument 1 is worked within a bone cavity (not shown), the bone tissue, for example, the spongiosa, is peeled from the bone by the teeth 3 and passes through the openings 10 into the interior of the working region 2 of the instrument 1. As indicated in FIG. 2, the interior of the working region 2 provides a relatively large space to receive the peeled material. Thus, clogging of the teeth 3 does not occur. Thus, the cutting edges 9 of the teeth can remain unencumbered. As indicated in FIG. 3, each tooth 3 projects over the respective opening 10 so that the peeled material can be readily directed into the interior of the instrument.

Referring to FIG. 1, the distal end of the instrument 1 may also be formed with a cutting edge 11 about the opening thereat.

Referring to FIG. 4, wherein like reference characters indicate like parts as above, the elongated hollow body of the instrument may be formed as a two-part structure. In this case, the proximal part constitutes the working region 2 while the distal part 12 forms a toothless smooth guide body. Such an instrument is preferred, for example, in shafts which are anchored in the proximal region and, in which, the distal part is circular in cross section and solely forms a slide guide approximately free of force transmission. Alternatively, the distal part 12 may be formed with teeth and openings in the same manner as the proximal part 2.

The connection of the parts 2, 12 may take place, for example, via a threaded stem 13 which is secured in a disk-shaped end 14 of the proximal part 2 or distal part 12. An associated female thread 16 then carries a further end plate 15 in the other part, i.e. the distal part 12 or proximal part 2.

The invention thus provides a rasp-like reaming instrument which can be readily used for preparing a long bone for implantation of an implant shape.

Further, the invention provides a reaming instrument wherein the material which is peeled from the interior of the bone can be taken up by a hollow interior of the instrument in order to prevent clogging of the teeth of the instrument.

What is claimed is:

1. A rasp-like reaming instrument for bones comprising
    an elongated hollow body of slender shape adapted to the shape of a prosthesis to be implanted in a bone;
    a plurality of circumferentially disposed openings in said body; and
    a plurality of circumferentially disposed teeth on said body for peeling bone material from within a bone, each said tooth having one of said openings adjacent thereto to permit passage of peeled bone material into said hollow body.

2. An instrument as set forth in claim 1 wherein said hollow body is formed on a plurality of discrete plates welded together along butt edges thereof.

3. An instrument as set forth in claim 1 which further comprises a distal part secured to said body to form a guide part.

4. An instrument as set forth in claim 1 wherein said distal part has a toothless exterior.

5. An instrument as set forth in claim 1 wherein each tooth has a sharp cutting edge disposed in projecting relation over a respective opening.

6. An instrument as set forth in claim 1 wherein said body has a cutting edge at a distal end thereof.

7. A rasp-like reaming instrument for bones comprising
    an elongated hollow body;
    a plurality of circumferentially disposed openings in said body;
    a plurality of circumferentially disposed teeth on said body for peeling bone material from within a bone, each said tooth having one of said openings adjacent thereto to permit passage of peeled bone material into said hollow body; and
    an upper arcuate part secured to said body to form an anvil for a driving instrument.

8. An instrument a set forth in claim 7 wherein said hollow body is conically shaped to taper inwardly towards a distal end.

9. A rasp-like reaming instrument for bones comprising
    an elongated hollow body conically shaped to taper inwardly towards a distal end;
    a plurality of circumferentially disposed openings in said body; and
    a plurality of circumferentially disposed teeth on said body for peeling bone material from within a bone, each said tooth having one of said openings adjacent thereto to permit passage of peeled bone material into said hollow body.

* * * * *